United States Patent
Gerrard

(10) Patent No.: US 9,335,272 B2
(45) Date of Patent: May 10, 2016

(54) TESTING MECHANICAL HARDWARE FOR WEAR AND A COMPOSITION

(75) Inventor: Darren Gerrard, Victoria (AU)

(73) Assignee: The Commonwealth of Australia, Canberra (AU)

( * ) Notice: Subject to any disclaimer, the term of this patent is extended or adjusted under 35 U.S.C. 154(b) by 317 days.

(21) Appl. No.: 13/133,876

(22) PCT Filed: Dec. 9, 2009

(86) PCT No.: PCT/AU2009/001597
§ 371 (c)(1),
(2), (4) Date: Jul. 11, 2011

(87) PCT Pub. No.: WO2010/065997
PCT Pub. Date: Jun. 17, 2010

(65) Prior Publication Data
US 2011/0263032 A1    Oct. 27, 2011

(30) Foreign Application Priority Data
Dec. 9, 2008   (AU) .................................. 2008906354

(51) Int. Cl.
*G01N 33/20* (2006.01)
*G01N 21/78* (2006.01)
*G01N 3/56* (2006.01)
*G01N 21/88* (2006.01)
(Continued)

(52) U.S. Cl.
CPC ................ *G01N 21/78* (2013.01); *G01N 3/56* (2013.01); *G01N 21/8803* (2013.01); *G01N 21/3103* (2013.01); *G01N 21/91* (2013.01); *G01N 31/22* (2013.01); *G01N 33/0045* (2013.01); *G01N 33/1813* (2013.01); *G01N 33/20* (2013.01); *G01N 33/84* (2013.01); *G01N 2203/0652* (2013.01)

(58) Field of Classification Search
CPC ... G01N 31/22; G01N 33/20; G01N 33/1813; G01N 33/0045; G01N 21/78; G01N 21/3103; G01N 33/84; C02F 1/72; C02F 11/086; C07D 213/72; C07F 15/0026; A61K 31/295; A61K 31/7016; A61K 33/26
USPC ............................................. 436/5, 6, 80, 84
See application file for complete search history.

(56) References Cited

U.S. PATENT DOCUMENTS 2,007,285 A * 7/1935 Schauffele ..................... 436/5
2,643,205 A * 6/1953 Murray ......................... 134/28
(Continued)

FOREIGN PATENT DOCUMENTS

WO    WO 2006/028941 A    3/2006

OTHER PUBLICATIONS

Standard Test Method for Corrosion of Surgical Instruments ASTM F1089-02 Feb. 2003.*

*Primary Examiner* — Krishnan S Menon
*Assistant Examiner* — Dwan A Gerido
(74) *Attorney, Agent, or Firm* — Frommer Lawrence & Haug, LLP

(57) ABSTRACT

The present invention discloses a method and composition for testing the wear on mechanical hardware. During the testing method a metal oxidant is applied the mechanical hardware being tested which deposits onto the mechanical and can be visually detected. One of the properties of the metal oxidant is that it is a substantially non-flow or non-drip medium that can be applied in situ with reduced risk to surrounding hardware.

20 Claims, 1 Drawing Sheet

(51) Int. Cl.
  *G01N 31/22* (2006.01)
  *G01N 33/18* (2006.01)
  *G01N 33/00* (2006.01)
  *G01N 21/31* (2006.01)
  *G01N 33/84* (2006.01)
  *G01N 21/91* (2006.01)

(56) References Cited

U.S. PATENT DOCUMENTS

| | | | |
|---|---|---|---|
| 3,549,993 A * | 12/1970 | Marsh et al. | 205/777 |
| 3,652,224 A * | 3/1972 | Johnson et al. | 436/5 |
| 4,311,738 A * | 1/1982 | Chi | 427/387 |
| 5,423,298 A * | 6/1995 | Pahis | F01C 1/3446 123/243 |
| 5,481,198 A * | 1/1996 | Patel | G01N 17/00 204/404 |
| 5,896,034 A * | 4/1999 | Marshall | G01N 27/205 204/404 |
| 6,054,038 A * | 4/2000 | Davis | G01N 17/02 204/404 |
| 2003/0188813 A1* | 10/2003 | Hirasawa et al. | 148/609 |
| 2009/0220689 A1* | 9/2009 | Bahls | 427/214 |

* cited by examiner

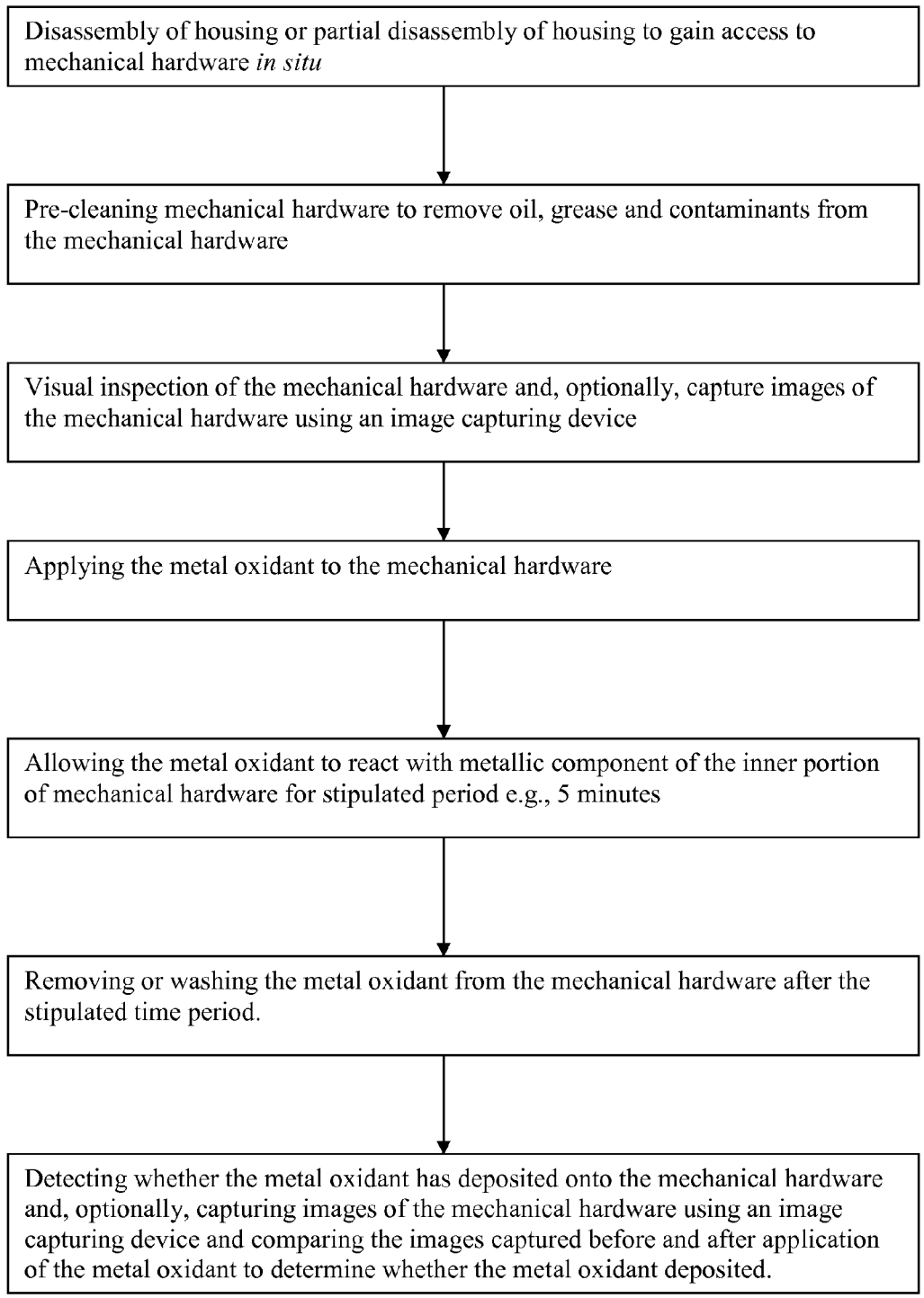

TESTING MECHANICAL HARDWARE FOR WEAR AND A COMPOSITION

This application is a 371 of PCT/AU2009/001597 filed on Dec. 9, 2009, published on Jun. 17, 2010 under publication number WO 2010/065997 A and claims priority benefits of Australian Patent Application Number 2008906354 filed Dec. 9, 2008, the disclosure of which is hereby incorporated by reference.

FIELD OF THE PRESENT INVENTION

The present invention relates to a method for testing the wear on mechanical hardware and a composition for testing the wear on mechanical hardware. In particular, the present invention relates to testing the wear on, or structural integrity of, mechanical hardware including metal or metal compounds such as iron containing compounds.

BACKGROUND OF THE PRESENT INVENTION

Monitoring the wear on mechanical hardware can be important in a range of different circumstances. For instance monitoring for wear on aircraft, such as drive shafts of the main gear box of helicopters and the rear rotor of helicopters should be conducted on a routine basis for safe and reliable operation.

In the case of helicopter drive shafts, silver plating is present over an inner high tensile steel core. Conventional testing techniques usually involve a simple visual inspection of the silver plating surface to detect where the silver plating has been removed. One of the difficulties of the conventional approach is that it can be difficult to differentiate between sections, particular small sections, where the silver plating has been removed and the inner steel core. This can create reliability issues in the test method.

Notwithstanding this difficulty, it is recognised that signs of wear and tear on the silver plating of helicopter drive shafts can occur prior to malfunction and possible catastrophic failure of the drive shaft.

The present invention is directed to an alternative technique for identifying the wear regions of the outer portion or coating of mechanical hardware.

SUMMARY OF THE PRESENT INVENTION

The present invention relates to a method of testing for wear on mechanical hardware having an inner portion that includes a metallic component and an outer portion that is substantially free of the same metallic component of the inner portion, the method including the steps of:
 a) applying metal oxidant to part of the mechanical hardware being tested so that the metal oxidant, in regions in contact with the metallic component, oxidises the metallic component of the inner portion and deposits on the mechanical hardware, and wherein the metal oxidant is non-flowing or is a non-flowing medium that can substantially retain shape when applied to non-horizontal surfaces of the mechanical hardware including inclined surfaces, upright surfaces and downwardly facing surfaces; and
 b) detecting the presence of the metal oxidant that has been deposited on the mechanical hardware.

In other words, the metal oxidant has a lower oxidation potential than the metallic component of the inner portion of the mechanical hardware. In this case, the metallic component of the inner portion acts as the reducing agent. The metal oxidant may contact the inner portion in regions where the outer portion of the mechanical hardware is absent, for example, the outer portion has been worn, eroded, removed, corroded or deteriorated by any means.

Throughout this specification, the term "mechanical hardware" encompasses any mechanical or physical component including drive shafts, gears, or any other static or dynamic component to which a load is applied.

Throughout this specification, the term "inner portion" embraces any substrate including an inner region or an inner core of the mechanical hardware. Similarly, throughout this specification, the term the "outer portion" embraces any outer layer, outer face or outer coating or alike.

The present invention also relates to a composition for testing the wear on mechanical hardware, the composition comprising:
 a metal oxidant that can oxidise a metallic component of an inner portion of the mechanical hardware and in turn precipitate onto the mechanical component; and
 an acid.
wherein the composition is non-flowing and is able to substantially retain shape on non-horizontal surfaces of the mechanical hardware including inclined surfaces, upright surfaces or downwardly facing surfaces at ambient temperatures

DETAILED DESCRIPTION

The metallic component of the inner portion may be any inorganic or metal containing constituent including elemental metal, ionic metal or compounds containing metal. For example, the metallic component may or may not include iron or iron containing compounds. The table below includes examples of the different types of metals that may be included in the inner portion of the mechanical hardware and corresponding metal oxidants.

TABLE 1

| Group | METALLIC COMPONENT OF THE INNER PORTION OF THE MECHANICAL HARDWARE | METAL OXIDANT (may comprise any one or a combination of the metal species listed below) |
|---|---|---|
| A | Iron | copper or nickel or tin |
| B | Copper | silver or gold or cadmium or lead or nickel |
| C | Zinc | copper or nickel or silver or tin |
| D | aluminium or magnesium | chromium |

For example, in the situation in which the inner portion of the mechanical component is steel i.e., including iron, the metal oxidant may include copper, nickel, tin or compounds thereof according to Group A in Table 1. In another example in which the inner portion of the mechanical component includes copper or copper containing compounds, the metal oxidant may include silver, gold, cadmium, lead, nickel or compounds thereof according to Group B in Table 1. In another example in which the inner portion of the mechanical component includes zinc or zinc containing compounds, the metal oxidant may include copper, nickel, silver, tin or compounds thereof according to Group C in Table 1. In yet another embodiment in which the inner portion of the mechanical component includes: aluminium, aluminium containing compounds, magnesium or magnesium containing compounds, the metal oxidant may include chromium or compounds thereof according to Group D in Table 1.

Although it is possible that the metal oxidant may be any type of suitable metal such as tin, gold, lead, nickel or chromium; suitably the metal oxidant is ionic, and even more suitably ionic copper such as $Cu^{2+}$.

Suitably, the outer coating is substantially free of the same type of metal as the metal oxidant. In the situation in which the metal oxidant is ionic copper, suitably the outer coating is substantially free of the copper or does not have a copperous appearance i.e., an orange or reddish appearance.

One of the advantages of the present invention is that the metal oxidant deposits enable sections in which the outer coating has been worn or eroded to be readily identified by comparison to the outer coating. For instance, in the situation in which the mechanical component has an outer silver plating, copper deposited on sections where the plating has been eroded or worn can be visually identified due to a colour differentiation between the plating and the deposit, and thereby provide an indication of the level of wear on the drive shaft.

In the situation where an undesirable level of metal oxidant has been deposited and thereby indicating a high level of wear on the mechanical hardware, the hardware can either be repaired, or replaced with fresh hardware as desired.

The metal oxidant may be provided as a viscous medium such as a gel or paste medium that may be manually spread or applied in globules. Suitably, the metal oxidant is provided as an immobilised medium that is non-flowing or non-dripping and can retain its shape over any desired operating temperatures including operating temperatures ranging of up to 50, 60 or even 70° C. but most desirably at ambient room temperature such as 20 to 40° C. Moreover, suitably the metal oxidant can be manually applied to mechanical components over horizontally oriented surfaces, and non-horizontal surfaces including upright surfaces, vertically oriented surfaces, and even downwardly facing surfaces and substantially retain its position, shape and form on the mechanical hardware without flowing, dripping or spreading under gravity.

According to an embodiment the step of applying the metal oxidant may involve applying the metal oxidant to the mechanical hardware while in situ. In other words, one of the benefits of the non-flowing properties of the metal oxidant is that when in use, the mechanical hardware can substantially remain in an in-use or operative position without the metal oxidant contacting other hardware not being tested. In some situations it may be necessary to disassemble or remove other components including housings to gain access to the hardware component being tested in situ. For instance, the metal oxidant can be applied to the drive shafts, such as a drive shaft of the rotor of a helicopter without detaching the drive shaft from the helicopter or without fully disassembling the gear box or drive train. In the past, it was necessary to disassemble sections of the helicopter gear boxes and drive shafts to isolate the components being tested from the other mechanical parts that do not have an outer coating that can protect the inner core from oxidation or reaction with the metal oxidant.

The metal oxidant or composition may include any suitable gelling agent including gelatine, agar, silica agents, resins or polymeric agents and so forth. An example of a suitable gelling agent is Surgilube™.

In an embodiment, the metal oxidant includes agar in the range of the 5 to 150 g/l, and suitably in the range of 10 to 50 g/l and even more suitably in the range of 10 to 30 g/l. An example of a suitable gelling agent is Agar Bacteriological (Agar No. 1) Product code LP0011 which is available from Oxoid Australia Pty Ltd.

In another embodiment, the metal oxidant may be paste or other viscous material.

Although it is possible that the metal oxidant may include ionic copper as part of an ion exchange material such as an ion exchange resin, suitably the ionic copper is in the form of an ionic copper salt complex, and more suitably is in the form of copper sulphate including either hydrated or anhydrous copper sulphate.

In an embodiment, the metal oxidant includes up to 100 g/l of copper sulphate and suitably 30 g/l copper sulphate. Even more suitably, the metal oxidant includes approximately 15 g/l copper sulphate.

Suitably, the metal oxidant or composition is acidified and has a pH of less than 7.0, and suitably a pH in the range of 1 to 6, and even more suitably in the range of 2 to 5. We have found that when acidified, the metal oxidant is able to more reliably deposit onto the inner portion of the mechanical hardware.

Suitably, the metal oxidant may be provided with or includes any one or a combination of different acids including sulphuric acid, nitric acid, hydrochloric acid and phosphoric acid.

In an embodiment, the metal oxidant or composition may be provided with or includes concentrated sulphuric acid at 98% v/v at an amount in the range of 0.1 to 5.0 ml/l. Even more suitably, sulphuric acid at 98% v/v is provided at approximately 0.5 ml/l.

Ionic copper will preferentially deposit, to larger degrees on sections of exposed metallic components of the inner portion of the mechanical hardware for example, a steel inner portion of the drive shaft. In some situations, for example, when the outer portion is conductive, copper may also deposit on the outer portion of the mechanical component. However, it is envisaged that by limiting the period of application of the metal oxidant, the deposition of copper will be most prevalent in sections in which the metal oxidant can penetrate the outer portion and contact the inner portion.

In an embodiment, the step of applying the metal oxidant includes applying the metal oxidant for a period of in the range of up to 60 minutes (or 1 to 60 minutes), or more suitably in the range of 5 to 10 minutes, and yet even more suitably for a period of approximately 5 minutes.

In an embodiment, the method includes a pre-cleaning step in which the mechanical component is cleaned to remove grease, oil and contaminants. The purpose of the pre-step is to allow the gel composition to contact and react with the metal face of the mechanical component. Any type of cleaning solution may be used in the pre-cleaning step including soaps, detergents or solvent based solutions including solutions containing hydrocarbons.

In an embodiment, the outer portion is any colour other than a yellow, gold, copper or green. More suitably, the outer portion has a black, silver, blue, grey or red coloured coating. It is also possible that the outer portion may be in the form of a metallic coating, polymeric material, paint or any other suitable material.

The step of detecting the presence of deposits of the metal oxidant may be carried out with the naked eye or with assistance of optical analysis equipment such as a magnifying glass and may also include the use of image capturing or recording devices such as digital cameras for digital photographic analysis or digital pixel analysis for comparing the surfaces of the mechanical component before and after the test.

In an embodiment, step b) includes capturing an image of the part of the mechanical hardware being tested using an image capturing device before the metal oxidant is applied thereto according to step a), capturing an image of the section of the mechanical hardware after the metal oxidant has been removed therefrom, and step b) includes comparing the images to detect the presence of the metal oxidant deposited.

The step of detecting the presence of the metal oxide deposited may be carried out in ambient daylight, or alternatively, may also be carried using a light source or lamp as desired, particularly if being carried out during the night.

One of advantageous characteristics of the metal oxidant is that it does not cause hydrogen embrittlement to high strength steels under the conditions described for its use by slow strain rate tensile testing in line with ASTM F519 (American Society of Testing and Materials).

Other Embodiments

An embodiment of the present invention relates to a method of testing or monitoring for wear on a mechanical component having one or more than one inner core that contains a metal and an outer coating that is substantially free of the same metal containing constituent such as, but by no means limited to, helicopter drive shafts having a steel inner core and an outer silver plating, the method including the steps of:
a) applying a viscous composition containing an ionic metal oxidant to the mechanical component, wherein at positions where the outer coating has been removed or deteriorated, the metal oxidant oxidises the metal of the inner core and deposits on the mechanical component; and
b) detecting the presence of metal oxidant deposited on the mechanical component from the viscous composition.

In yet another embodiment, the present invention relates to a method of testing for wear on mechanical hardware having an inner portion that includes a metallic component and an outer portion that is substantially free of the same metallic component of the inner portion, the method including the steps of:
a) applying an oxidant to part of the mechanical hardware being tested so that the metal oxidant, in regions in contact with the metallic component, oxidises the metallic component of the inner portion and deposits on the mechanical hardware, and wherein the oxidant is non-flowing or is a non-flowing medium that can substantially retain shape when applied to non-horizontal surfaces of the mechanical hardware including inclined surfaces, upright surfaces and downwardly facing surfaces; and
b) detecting the presence of the oxidant that has been deposited on the mechanical hardware.

In yet another embodiment, the present invention relates to a composition for testing the wear on mechanical hardware, the composition comprising:
an oxidant that can oxidise a metallic component of an inner portion of the mechanical hardware and in turn precipitate onto the mechanical component; and
an acid,
wherein the composition is non-flowing and is able to substantially retain shape on non-horizontal surfaces of the mechanical hardware including inclined surfaces, upright surfaces or downwardly facing surfaces The oxidant may be a non-metallic oxidant or an organic oxidant such as polymeric oxidant. However suitably, the oxidant is a metallic or inorganic oxidant.

An embodiment of the present invention relates to composition for testing the wear on mechanical components, the composition comprising:
a gelling agent, suitably in the form of agar;
a metal ionic oxidant, suitably in the form of a copper ionic complex; and
an acid
wherein the metal oxidant acts as a oxidant to mechanical components containing solid elemental iron such that the metal oxidant will precipitate out of the composition onto the iron containing substrate.

An embodiment of the present invention also relates to use of the composition to test for the wear on the mechanical components, wherein the mechanical component has an outer portion that is substantially free of the type of metal of the metal oxidant of the composition and the mechanical component has an iron containing inner portion that is covered by the outer portion.

An embodiment of the present invention relates to a method of testing or monitoring for wear on mechanical components having one or more than one inner portion that contains iron containing constituents and an outer portion that is substantially free of iron such as, but by no means limited to, helicopter drive shafts having a steel inner core and an outer silver plating, the method including the steps of:
a) applying an ionic metal oxidant to the outer portion of the mechanical component, wherein at positions at which the outer coating has been removed or deteriorated, the metal oxidant oxidises the iron of the inner portion and deposits on the mechanical component; and
b) detecting the presence of metal oxidant deposits on the mechanical component.

An embodiment of the present invention relates to a method of testing or monitoring for wear on mechanical components having an inner portion that contains iron containing constituents and an outer portion that is free of iron containing constituents such as, but by no means limited to, helicopter drive shafts having a outer silver plating on an inner steel core, the method including the steps of:
a) applying a gel or paste material containing ionic copper constituents to the outer portion of the mechanical component, wherein at positions on the mechanical component in which the outer portion has been removed or eroded the ionic copper constituents deposit on the mechanical component; and
b) detecting the presence of copper deposits on the mechanical component.

An embodiment of the present invention relates to a method of making a composition, including:
dissolving a metal oxidant in heated water to form a solution;
adding an acid to the solution;
adding a gelling agent to the solution to form a composition;
cooling the composition so that the composition become a non-flowing or a non-dripping composition.

The method of making the composition described in the paragraph immediately above may also include any one or combination of feature of the composition of the present and embodiments thereof in this specification.

Example

The present invention will now be described with reference to a non-limiting example.

Approximately 15 g/l of copper sulphate pentahydrate was dissolved in 500 ml of distilled water to form a copper sulphate solution. A diluted sulphuric acid solution, approximately 10% v/v, was then prepared by pipetting 10 ml of concentrated sulphuric acid (98%) into 100 ml of distilled water. 5 ml of the diluted acid solution (10% v/v) was then pipetted into the copper sulphate solution and the total volume made up to 1000 ml by adding distilled water. The acidified copper sulphate solution was then heated to approximately 90° C. with stirring and 30 g of Agar Bacteriological (Agara no. 1) quickly added while stirring and dissolved. The metal oxidant composition was then cooled to allow the gel to set. The makeup of the composition may be summarised as follows.

TABLE 2

| Metal Oxidant Composition | Amount of total composition |
|---|---|
| Gelling agent (Agar) | 30 g/l |
| Copper sulphate ($CuSO_4 \cdot 5H_2O$) | 15 g/l |
| Sulphuric acid (98% w/v) | 0.5 ml/l |

A suitably gelling agent is Agar Bacteriological (Agar No. 1), Product Code LP0011 and is available from Oxoid Australia Pty Ltd, 20 Dalgleish Street, Adelaide, South Australia, 5031.

The resulting composition was a thick paste-like medium that was capable of retaining its shape when applied to non-horizontal surfaces including vertical surfaces and downward facing surfaces. The composition may be applied in globules or spread over the surface using blade.

The composition was then performance tested by being spread on the silver plated surfaces of the helicopter tail rotor drive shaft while in-situ. Prior to application of the composition, the silver plating of the drive shaft was pre-cleaned to remove grease, oil and other contaminants. This step is important and ensures that the composition contacts the steel or iron surface of the drive shaft. If the pre-cleaning step is not completed, a false testing of "no" copper deposit is possible which could lead one to conclude the mechanical component is not worn when in fact it should be repaired or replaced. The pre-cleaning step may be carried out using any water or hydrocarbon based solvent. An example of a suitable pre-cleaner is an aviation solvent sold by Chemetall under the trade name Ardrox 9PR50C. Following the cleaning step, the silver plating of the drive shaft was visually analysed by the naked eye to assess the condition of the silver plating, and in particular identify, or at least attempt to identify, regions in the silver plating that had been removed.

The metal oxidant composition was then applied at a suitable thickness to the surface being tested. For example, a thickness in the range of 0.1 up to approximately 20 mm can be applied and allowed to remain on the drive shaft for a period of approximately 5 to 10 minutes. At the end of this period the composition was removed from the drive shaft with a wet cloth and washed with water.

The ionic copper in the composition acts as an oxidant and autocatalytically deposited on the steel drive shaft in regions where the silver plating had been removed. The copper precipitant enabled the location and degree of the wear to the silver plating to be more accurately located and revealed damaged silver plating that may not have been detected by the naked eye.

DRAWING

FIG. 1 is a block diagram summarising the basic steps that may be undertaken in testing mechanical hardware. The steps include the following. i) If necessary, housing or parties of a vehicle surrounding the mechanical hardware to be tested may be disassembled. ii) The mechanical hardware may be cleaned to remove oil, grease and contaminants. iii) Once cleaned, the mechanical hardware may be visually inspected and, optionally, images of the hardware may be taken using a digital camera. iv) The metal oxidant is then applied to parts of the mechanical hardware being tested and allowed to react for approximately 5 minutes. v) The gel composition is then washed or removed. vi) The metal oxidant deposited is then observed.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The invention claimed is:

1. A method of testing for wear on mechanical hardware, the method including the steps of:
   a) accessing mechanical hardware in the form of either a helicopter drive shaft or a helicopter gear while substantially in an in-use or operative position, the mechanical hardware having an inner portion including an iron containing component and an outer portion containing silver and substantially free of the iron containing component of the inner portion;
   b) applying metal oxidant to the mechanical hardware while substantially remaining in the in-use or operative position, the metal oxidant including an ionic copper salt complex, and the metal oxidant being applied in at least regions wherein the inner portion is exposed through the outer portion to oxidize the iron containing component of the inner portion and deposit on the mechanical hardware without oxidizing the outer portion, and wherein the metal oxidant is non-flowing so as to substantially retain shape when applied to non-horizontal surfaces of the mechanical hardware including inclined surfaces, upright surfaces and downwardly facing surfaces so the metal oxidant is capable of being prevented from contacting other hardware not being tested; and
   c) detecting wear of the outer portion based on detecting deposits of the metal oxidant on the inner portion.

2. The method according to claim 1, wherein the metal oxidant includes at least one of elemental, ionic, or compounds of copper, nickel, or tin.

3. The method according to claim 1, wherein the metal oxidant has a lower oxidation potential than iron or iron containing compounds such that the metal oxidant can oxidise iron of the iron containing component and precipitate onto the mechanical component.

4. The method according to claim 1, wherein the outer portion is substantially free of the same type of metal as the metal oxidant.

5. The method according to claim 1, wherein the outer portion is substantially free of copper or copper containing compounds, or does not have a cupreous appearance including an orange or reddish appearance.

6. The method according to claim 1, wherein the metal oxidant includes copper sulphate in an amount up to 50 g/l.

7. The method according to claim 1, wherein the step of detecting the presence of metal oxidant deposited on the mechanical hardware is performed with the unaided or naked eye.

8. The method according to claim 1, wherein step a) includes the metal oxidant being applied to the mechanical hardware for a period of up to 60 minutes and after which, the metal oxidant is removed from the mechanical hardware prior to step b).

9. The method according to claim 1, wherein the method includes capturing an image of the part of the mechanical hardware using an image capturing device before the metal oxidant is applied thereto according to step a), and capturing an image of the part of the mechanical hardware after the viscous composition has been removed therefrom, and step b) includes comparing the images to detect the presence of the metal oxidant deposited.

10. The method according to claim 1, wherein the metal oxidant is provided with a pH in a range of 1 to 6.

11. The method according to claim 1, wherein the metal oxidant is provided with concentrated sulphuric acid (98% v/v) in the range of 0.01 to 5.0 ml/l.

12. The method according to claim 1, wherein the metal oxidant is provided in a paste medium.

13. The method according to claim 1, wherein the method includes a pre-cleaning step in which the mechanical hardware is cleaned to remove grease, oil and contaminants therefrom.

14. The method according to claim 13, wherein the pre-cleaning step is carried out using any one or a combination of soaps, detergents or solvent based solutions including hydrocarbons based solvents.

15. The method according to claim 1, wherein step a) includes the metal oxidant being applied to the mechanical hardware for a period up to approximately 5 minutes and after which, the metal oxidant composition is removed from the mechanical hardware prior to step b).

16. The method according to claim 15, wherein the method includes removing the metal oxidant from the mechanical hardware by rinsing with the mechanical hardware with water.

17. The method according to claim 1, wherein the metal oxidant is provided in a gel medium.

18. The methods according to claim 17, wherein the gel medium includes any one or combination of gelatine, agar, silica agents, resins or polymeric gelling agents.

19. The method according to claim 18, wherein the gel medium includes up to 150 g/l of agar.

20. A method of testing for wear on mechanical hardware the method including the steps of:
a) accessing mechanical hardware in the form of either a helicopter drive shaft or a helicopter gear while in a substantially in-use or operatative position, the mechanical hardware having an inner portion including an iron containing component and an outer coating that contains silver and is substantially free of the iron containing, the outer coating protecting the inner core from oxidiation,
b) pre-cleaning the mechanical hardware to remove grease or oil therefrom;
c) visually inspecting the mechanical hardware to form a preliminary assessement of regions in which the outer coating has been removed;
d) applying metal oxidant to the mechanical hardware while substantially remaining in an in-use or operative position, the metal oxidant including an ionic copper salt complex and an acid in the form of either sulphuric acid and/or nitric acid, and the metal oxidant being applied in at least regions wherein the inner portion is exposed through the outer coating and wherein the metal oxidant is non-flowing so as to substantially retain shape when applied to non-horizontal surfaces of the mechanical hardware including inclined surfaces, upright surfaces and downwardly facing surfaces, the non-flowing property of the oxidant capable of preventing the metal oxidant flowing onto and contacting other hardware not being tested;
e) allowing the metal oxidant to oxidize the iron containing component of the inner portion for a stipulated time period and deposit copper onto the inner portion of the mechanical hardware where the outer coating of the mechanical hardware is absent without oxidizing the outer portion;
f) washing the metal oxidant from the mechanical hardware after the stipulated time period; and
g) detecting wear of the outer coating based on detecting deposits of the metal oxidant on the inner portion in comparison to the outer coating.

* * * * *